United States Patent
Koch et al.

(10) Patent No.: US 7,413,031 B2
(45) Date of Patent: Aug. 19, 2008

(54) APPARATUS AND METHOD FOR MAINTAINING CONTROL OF A DRILLING MACHINE

(75) Inventors: Geoff D. Koch, Perry, OK (US); Lee Widener, Perry, OK (US); David R. Payne, Perry, OK (US)

(73) Assignee: The Charles Machine Works, Inc., Perry, OK (US)

( * ) Notice: Subject to any disclaimer, the term of this patent is extended or adjusted under 35 U.S.C. 154(b) by 283 days.

(21) Appl. No.: 10/220,465

(22) PCT Filed: Jul. 18, 2001

(86) PCT No.: PCT/US01/22554

§ 371 (c)(1),
(2), (4) Date: Aug. 29, 2002

(87) PCT Pub. No.: WO02/06630

PCT Pub. Date: Jan. 24, 2002

(65) Prior Publication Data

US 2003/0205409 A1    Nov. 6, 2003

Related U.S. Application Data

(60) Provisional application No. 60/219,019, filed on Jul. 18, 2000.

(51) Int. Cl.
    *E21B 7/04* (2006.01)
(52) U.S. Cl. .............................. 175/24; 175/26; 175/27; 175/40; 175/53; 175/62
(58) Field of Classification Search .................. 175/19, 175/24, 26, 61, 62, 27, 40, 53; 180/315, 180/317; 173/4, 11, 2, 19; 702/9
    See application file for complete search history.

(56) References Cited

U.S. PATENT DOCUMENTS 3,385,376 A  *  5/1968  Hobhouse .................... 175/27
3,547,216 A     12/1970 Marie
3,708,031 A      1/1973 Jania et al.

(Continued)

FOREIGN PATENT DOCUMENTS

DE          2 137 693          2/1973

(Continued)

*Primary Examiner*—Richard E. Chilcot, Jr.
*Assistant Examiner*—Matt J Smith
(74) *Attorney, Agent, or Firm*—Tomlinson & O'Connell, PC

(57) ABSTRACT

An apparatus is provided for maintaining control of a machine which produces thrust, rotation or other outputs in response to input signals. The apparatus has two distinct parts, namely the operator input portion and the output portion. The operator input portion consists of the primary thrust, rotation and other output control, and the input signal generation, signal maintenance and signal resume control. Through these controls, the operator enters the desired operation at conditions and levels for rotation, thrust, and other input signals. The output portion consists of an information processing and control portion and the power units for rotation, thrust and other outputs generated from the machine. The information processing and control system interprets all of the desired operational conditions and levels from the input portion and sends commands to the thrust, rotation and other power units to produce the desired outputs in response to the input signals.

52 Claims, 12 Drawing Sheets

U.S. PATENT DOCUMENTS

| | | | |
|---|---|---|---|
| 4,165,789 A | 8/1979 | Rogers | |
| 4,400,935 A | 8/1983 | Louis | |
| 4,430,846 A | 2/1984 | Presley et al. | |
| 4,510,963 A | 4/1985 | Presley et al. | |
| 4,913,251 A | 4/1990 | Farr | |
| 5,147,010 A | 9/1992 | Olson et al. | |
| 5,161,634 A | 11/1992 | Ichihara et al. | |
| 5,348,115 A | 9/1994 | Devier et al. | |
| 5,564,455 A | 10/1996 | Keating et al. | |
| 5,713,422 A * | 2/1998 | Dhindsa | 175/27 |
| 5,746,278 A | 5/1998 | Bischel et al. | |
| 5,893,425 A * | 4/1999 | Finkle | 180/342 |
| 5,913,371 A | 6/1999 | Jenne | |
| 5,944,121 A | 8/1999 | Bischel et al. | |
| 5,961,252 A * | 10/1999 | Mercer et al. | 175/53 |
| 6,079,506 A | 6/2000 | Mercer | |
| 6,226,588 B1 | 5/2001 | Teramura et al. | |
| 6,237,711 B1 | 5/2001 | Hunt | |
| 6,256,574 B1 | 7/2001 | Prestl et al. | |
| 6,354,023 B1 * | 3/2002 | Trahan et al. | 701/50 |
| 6,357,537 B1 * | 3/2002 | Runquist et al. | 175/62 |
| 6,408,952 B1 * | 6/2002 | Brand et al. | 175/24 |

FOREIGN PATENT DOCUMENTS

| | | |
|---|---|---|
| DE | 2 315 077 | 10/1974 |
| DE | 35 13 750 1 A | 10/1986 |
| EP | 0 721 052 A2 | 7/1996 |
| GB | 2 335 450 A | 9/1999 |
| WO | WO 88/02435 | 4/1988 |
| WO | WO 98/16712 | 4/1998 |
| WO | WO 00/66386 | 11/2000 |

* cited by examiner

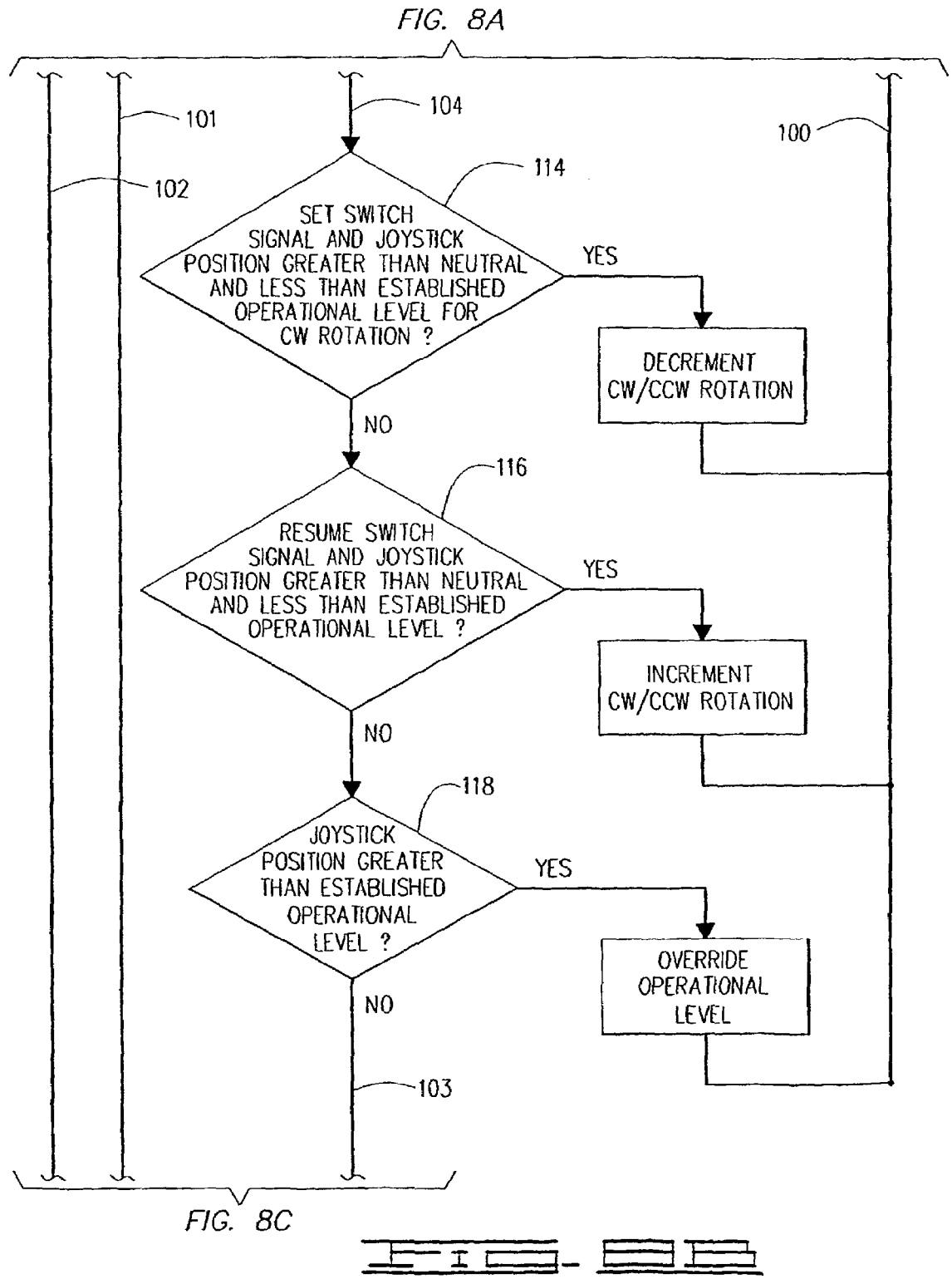

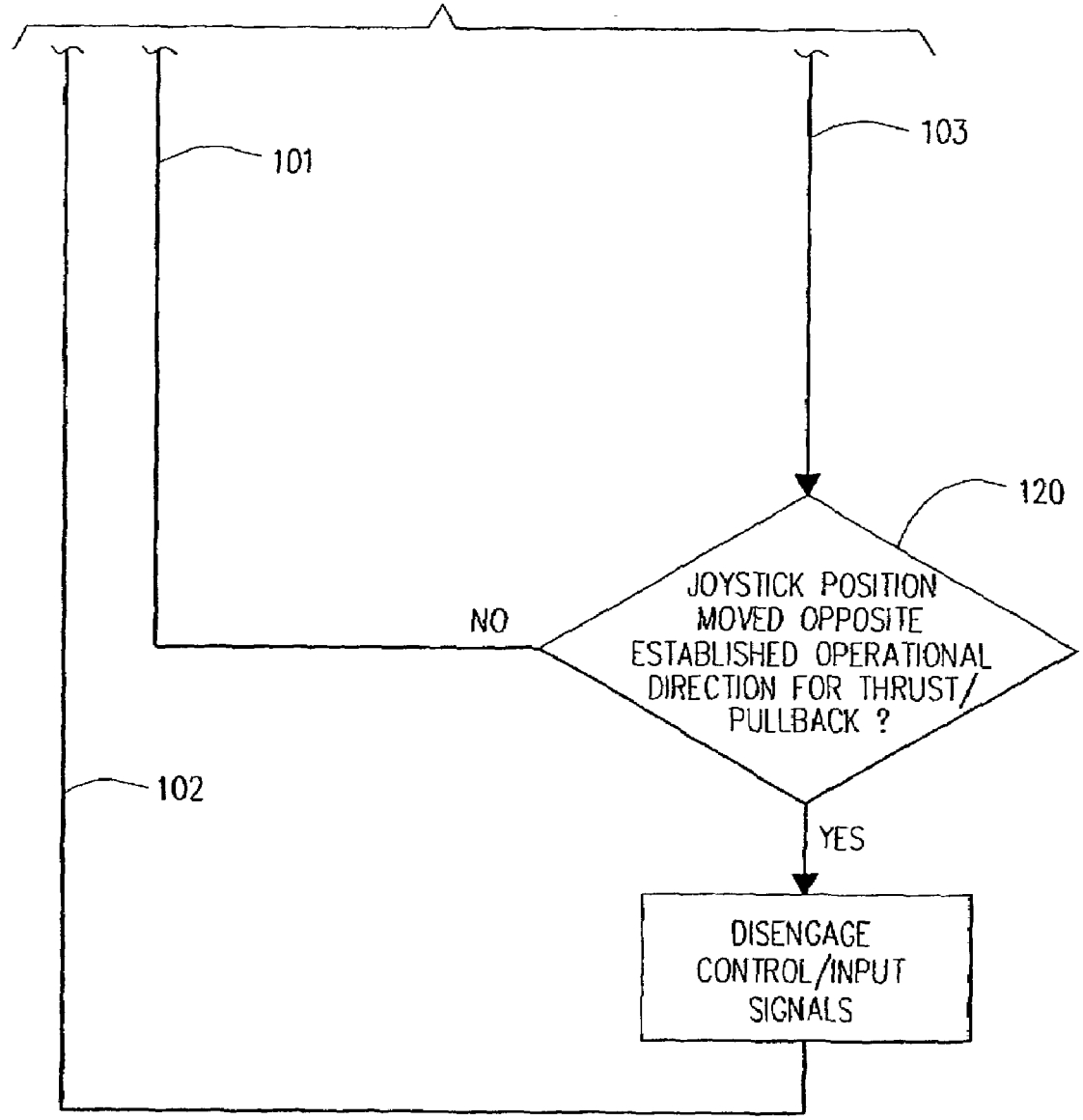

APPARATUS AND METHOD FOR MAINTAINING CONTROL OF A DRILLING MACHINE

CROSS REFERENCE TO RELATED APPLICATION

This application claims the benefit of U.S. Provisional Application No. 60/219,091, filed on Jul. 18, 2000, the contents of which are incorporated herein fully by reference.

FIELD OF THE INVENTION

The present invention relates to the field of horizontal directional drilling, and more particularly but not by way of limitation, to a control apparatus and associated method for maintaining control of the thrust or pullback, together with rotation of a horizontal directional drilling machine acting on a drill string to form a subterranean bore hole.

BACKGROUND OF THE INVENTION

Horizontal directional drilling machines are used to install underground utilities or other objects. This technology is gaining widespread favor because it minimizes ground surface disruption and the likelihood of damaging already-buried objects.

Horizontal directional drilling operations generally consist of using the drilling machine to advance a drill string through the subterranean earth along a preselected path. The path is ordinarily selected so as to avoid already-buried objects such as buried utilities. Certain aspects of the drilling machine and the manner with which it acts on the drill string are included in U.S. Pat. No. 6,085,852 and U.S. Pat. No. 5,799,740, the contents of both are fully incorporated by reference herein.

The drilling machine generally comprises a frame, an anchoring system, a drive assembly mounted to the frame and connectable to the uphole end of the drill string, and a bit connected to the downhole end of the drill string. The drive assembly provides thrust and rotation to the drill string which, in turn, thrusts and rotates the bit through the subterranean earth, forming a borehole. The drive assembly generally comprises one or more power sources for thrusting and rotating the drill string. The drill string is advanced in a substantially straight line direction by a simultaneous rotating and thrusting of the drill string by the drive assembly. To change the direction, conventional steering techniques are used such as those associated with a slant-faced bit. This type of bit is, after being oriented in the desired direction, advanced without drill string rotation to change course of the borehole. When the borehole is completed, typically the bit is replaced with a backreaming tool. Then the drive assembly is used to provide pullback force together with rotation to the drill string which, in turn, will pullback and rotate the backreamer back through the borehole to pack and finally size the borehole.

There are times when it is desirable to maintain the thrust and rotation applied to the drill string for a desired duration. This could be accomplished by manually stroking a control device such as an electric joystick or lever, hydraulic joystick or lever, or manual joystick or lever, to a desired position. Adjustments are made until the drilling machine is operating at a perceived optimum level. The operator then must try and maintain these operational levels by holding the joystick or lever in the desired position, often for long periods of time. When the operator releases the thrust and rotation control for any reason, such as to either add or remove a pipe segment to the drill string, the desired operational levels must be redetermined or located again by trial and error. Additionally, because of human fatigue and uncertainty of actual operational levels, it proves very difficult for an operator to maintain these operational levels for long periods of time.

Some recent useful improvements to controls on directional drilling units have included adding a speed limiting potentiometer on either the thrust or rotation circuits to set a new maximum thrust or rotation level when the joystick or lever is fully stroked. This setup still requires the operator to use the joystick or lever to control rotation or thrust but gives the operator better control of the operational levels in these conditions because the control limit can be set against a stop determined by the limit level set by the potentiometer. Setups of this type on directional drilling units have allowed successful drilling in hard ground conditions and rock where productive manual control previously was nearly impossible or, at best, very tedious. It has also been found to be effective with both conventional bits and mud motors. However, the operator must still hold the control device for extended periods of time. These events and others have led to the development of the s stem of the present invention.

SUMMARY OF INVENTION

The present invention comprises an apparatus and a method for operation of a control system.

In one aspect the invention is a system for controlling a machine which produces a thrust output in response to a thrust input signal and a rotation output in response to a rotation input signal. The system comprises a dynamic control system, a thrust maintenance system, a rotation maintenance system, a thrust interrupt system and a rotation-interrupt system. The dynamic control system is adapted to regulate the thrust input signal and the rotation input signal in response to dynamic user input. The thrust maintenance system is adapted to automatically maintain the thrust input signal at a user-selected thrust maintenance level in response to a thrust maintenance signal. Additionally, the rotation maintenance system is adapted to automatically maintain the rotation input signal at a user-selected rotation maintenance level in response to a rotation maintenance signal.

When it is desirable to discontinue automatic maintenance of either the thrust or rotation input signals, the system employs the thrust interrupt system and the rotation interrupt system, respectively. The thrust interrupt system is adapted to discontinue the automatic maintenance of the thrust input signal at the thrust maintenance level in response to a thrust interrupt signal. The rotation interrupt system is adapted to discontinue the automatic maintenance of the rotation input signal at the rotation maintenance level in response to a rotation interrupt signal.

In another aspect the invention is a system for controlling a drilling machine adapted to drivingly engage a drill string having a downhole tool. The drilling machine produces an output having a plurality of kinematic components, with each such output component responsive to a corresponding component input signal. The system comprises a dynamic control system, a component maintenance system and a component interrupt system. The dynamic control system is adapted to regulate each component input signal in response to dynamic user input. The component maintenance system is adapted to automatically maintain at least one component input signal at a user-selected component maintenance level in response to a component maintenance signal. When it is desirable to discontinue automatic maintenance of said component input signal, the system employs a component interrupt system adapted to discontinue the automatic maintenance of said component input signal in response to a component interrupt signal.

In yet another aspect, the invention is a system for controlling a drilling machine having a pipe handling assembly for adding and removing a plurality of pipe sections from a drill string. The machine produces a thrust output in response to a thrust input signal and a rotation output in response to a rotation input signal. The system comprises a dynamic control system, a maintenance system and an interrupt system. The dynamic control system is adapted to regulate the thrust input signal and the rotation input signal in response to dynamic user input. The maintenance system is adapted to automatically maintain at least one of the rotation input signal and the thrust input signal at a user-selected maintenance level for the same input signal in response to a maintenance signal.

When it is desirable to discontinue automatic maintenance of at least one of the rotation input signal and thrust input signal, the system employs an interrupt system adapted to discontinue automatic maintenance of the same input signal at the maintenance level for the said same input signal in response to an interrupt signal.

In still another aspect, the invention is a method for controlling a horizontal drilling machine having a drill string with a downhole tool. The method produces a thrust output in response to a thrust input signal and a rotation output in response to a rotation input signal. The method comprises selecting a subsurface bore path, regulating the thrust input signal and rotation input signal, automatically maintaining the thrust and rotation input signals respectively, and discontinuing the automatic maintenance of the thrust and rotation input signals respectively.

The selected subsurface bore path is the path along which the downhole tool is to be moved by axially advancing the drill string so as to move the downhole tool along at least a portion of the selected subsurface bore path. Regulating the thrust input signal and the rotation input signal is done in response to a dynamic user input. Automatically maintaining the thrust input signal at a user-selected thrust maintenance level is done in response to a thrust maintenance signal. Additionally, automatically maintaining the rotation input signal at a user-selected rotation maintenance level is done in response to a rotation maintenance signal.

Finally, discontinuing automatic maintenance of the thrust input signal at the thrust maintenance level is achieved in response to a thrust interrupt signal. Discontinuing automatic maintenance of the rotation input signal at the rotation maintenance level occurs in response to a rotation interrupt signal.

DETAILED DESCRIPTION OF THE PREFERRED EMBODIMENTS

Figure 1:
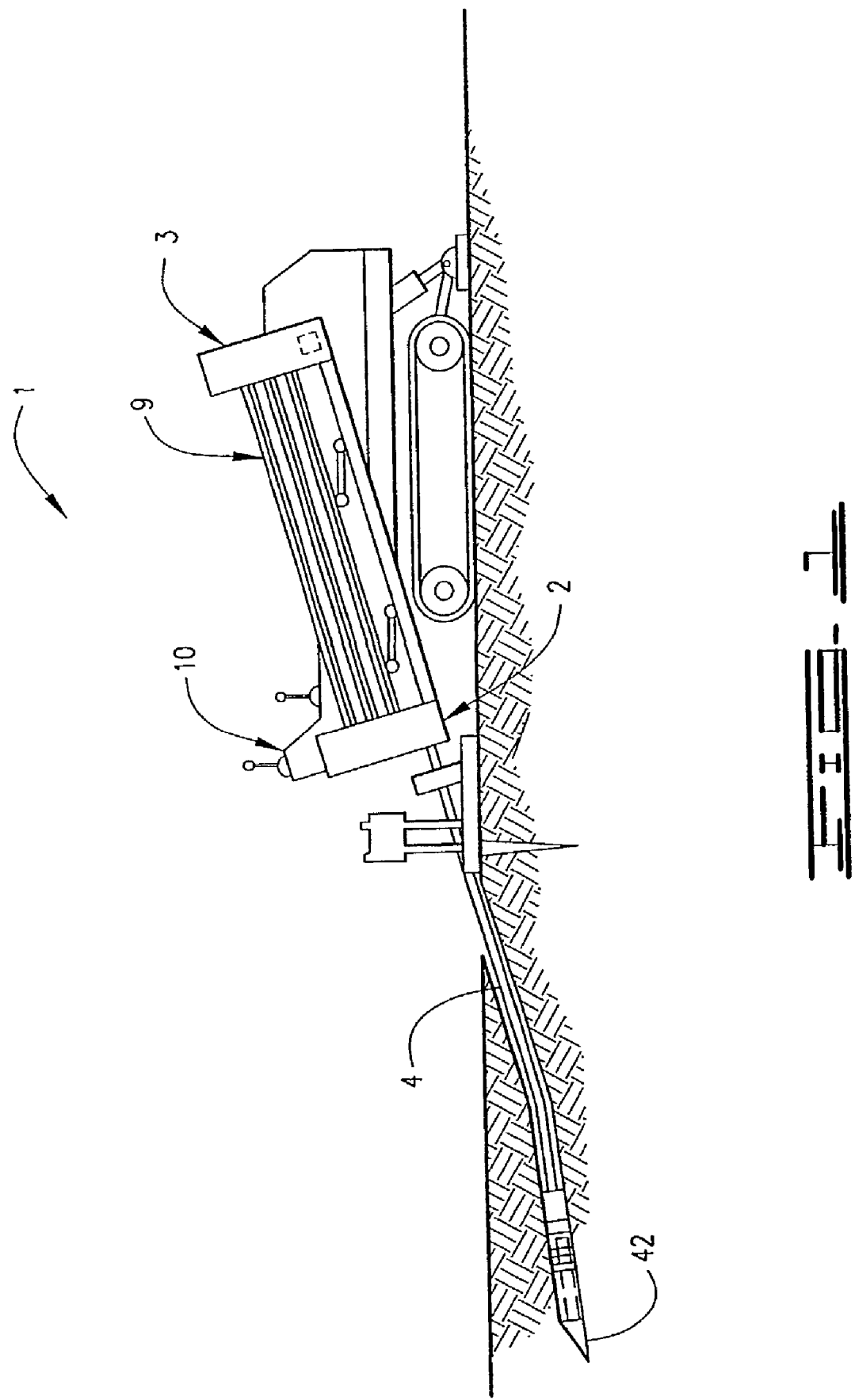
FIG. 1 is a diagrammatic representation of a horizontal drilling machine constructed in accordance with the present invention.

Generally, the present invention provides a system for maintaining control of a machine which generates varying outputs of thrust and rotation in response to control signals, typically thrust input signals or rotation input signals. The system has two distinct portions, namely, the operator input portion and the control and output portion. The operator input portion consists of primary thrust and rotation control and the adjustment control. Through these controls, the operator can enter the desired operational conditions and levels for rotation and thrust on a machine either singly or in combination. The control and output portion on the other hand, consists of a controller and proportional control valves for the thrust and rotation power units. The control system interprets all the desired operational conditions from the input portion and sends commands to the respective control valves of the power units to produce the desired outputs. However, it may be noted that the desired output may vary from the input with changes in load/environmental conditions.

The control system therefore, permits an operator of the machine to independently set, adjust, override, disengage, and resume operational levels for rotation and thrust outputs on the machine in response to input signals. That is, the operator manually determines what initial operational levels are desired for rotation and thrust outputs. These levels are then input into a control system for the machine through activation of one or more input devices (typically some type of electrical joystick or contact switches) located on the primary thrust and rotation control. After entering the operational levels into the control system, the operational levels can be adjusted up or down using the adjustment control. However, the control system may have the operational levels overridden through the primary thrust or rotation control. Additionally, the control system can be stopped through the use of an input through the primary thrust and rotation control or a separate interrupt control. Finally, the rate settable control system can be reinstated to the previous operational levels using the primary thrust and rotation control and the adjustment control.

The control system of the present invention can be adapted for use with any machine which generates an output having a plurality of kinematic components such as thrust, pullback, rotation, etc. For example, vertical drilling machines, trenching, plowing, horizontal drilling machines, etc. As way of illustration, the kinematic components for a trenching machine may include ground drive speed and digging chain speed. Turning now to the drawings in general and to FIG. 1 in particular, shown therein is a horizontal drilling machine 1 in accordance with the present invention. The drilling machine 1 preferably comprises a frame for supporting a drive system 2 (better seen in FIG. 2) and a pipe handling device 3. The drilling machine 1 further comprises a drill string 4 coupled to the drive system 2 at an uphole end of the drill string. Further, the drill string 4 has an underground tool attached to it at a downhole end of the drill string.

Figure 2:
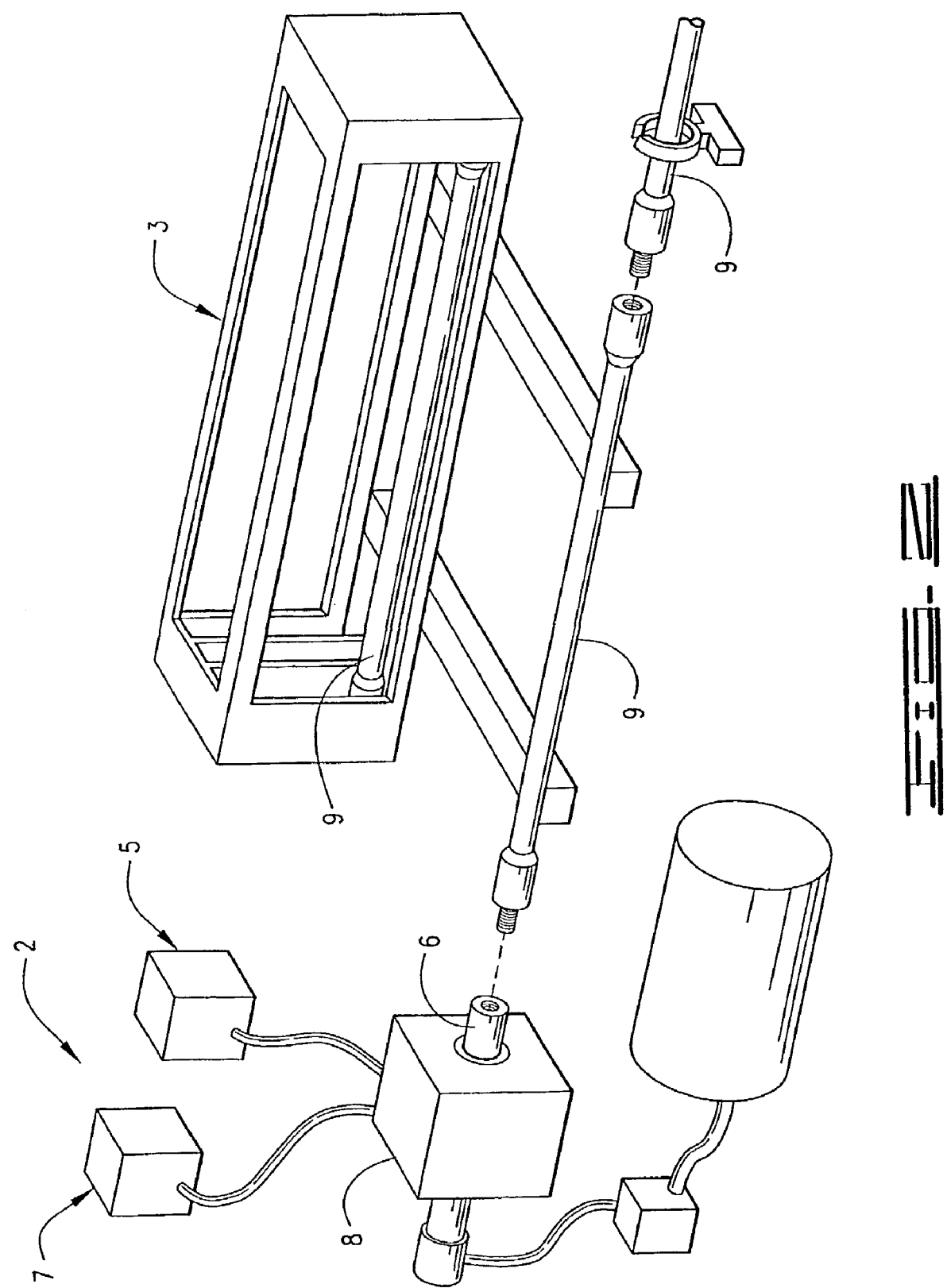
FIG. 2 is a diagrammatic representation of the drive system and the pipe handling device of the drilling machine of FIG. 1.
Figure 7:
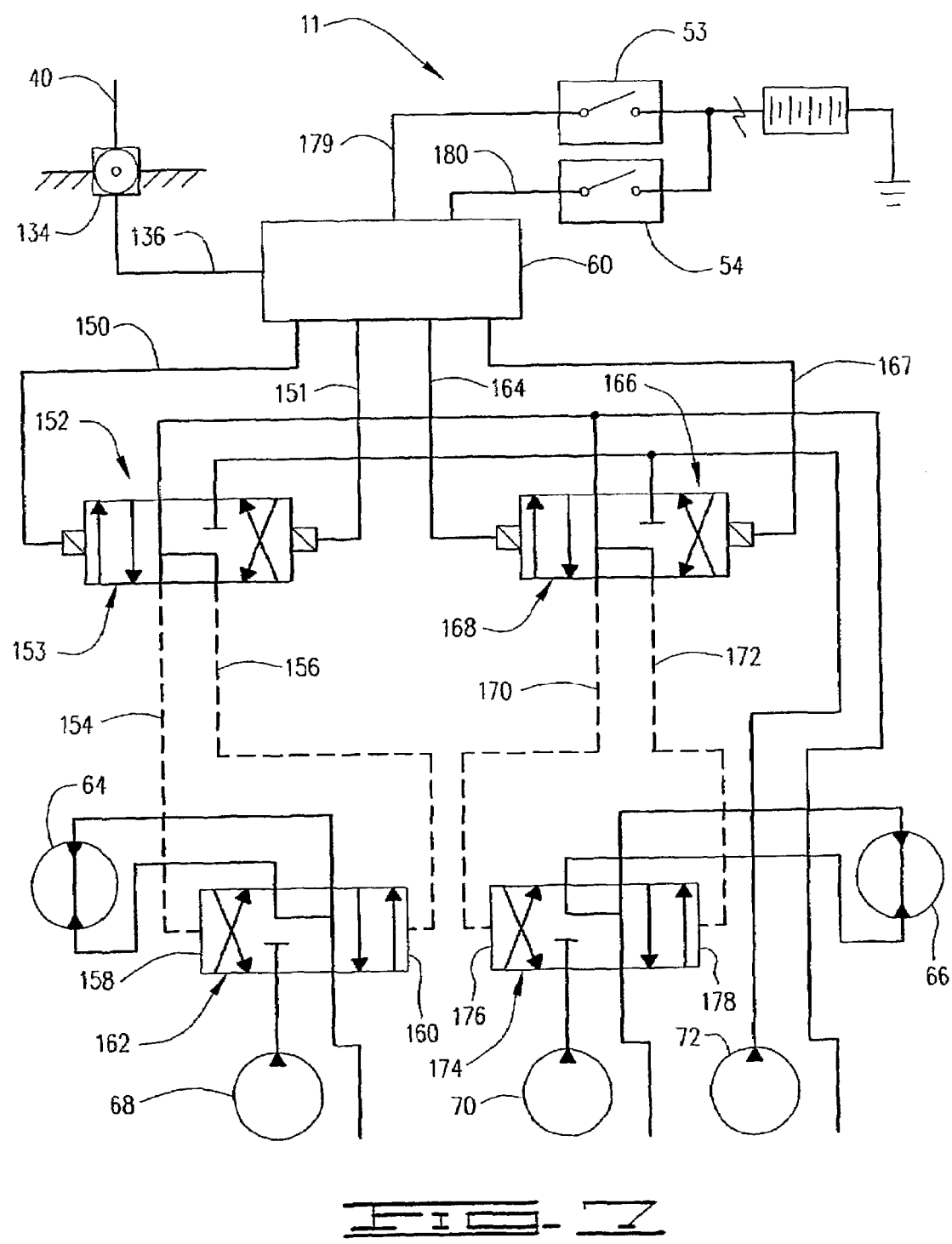
FIG. 7 is a schematic representation of a electro-hydraulic system constructed in accordance with an embodiment of the present invention.

With reference to FIG. 2, there is shown therein the components of the drive system 2. The drive system 2 generates and provides the power applied to the drill string 4 by the drilling machine 1. As will be explained more fully below, the drive system 2 comprises an engine and a plurality of hydraulic pumps or motors, valves (as shown in FIG. 7), and plumbing that supply power to the various components of the drilling machine 1. However, the invention contemplates the use of any system suitable for powering the components of the drilling machine 1. For example, electric or combustion powered equipment may be used for the engine and the plurality of sources supplying power to the components of the drilling machine 1. In an alternative embodiment, power sources such as fuel cells can be used to generate power locally for any of the various components of the drilling machine 1.

With continued reference to FIG. 2, the drive system 2 in this embodiment preferably comprises separate hydraulic motors for rotating and axially moving the drill string 4. As with other components of the drilling machine 1, an engine and hydraulic pumps (not shown) supply power needed to operate the hydraulic motors for powering rotation and axial movement through control valves as will be described in greater detail later in the discussion pertaining to FIG. 7. As used herein, the hydraulic motors together with the power source to operate the motors shall be collectively known as power units.

A rotation power unit 5 is operatively connected to a rotatable spindle 6 to drive rotation of the spindle. A thrust power unit 7 is operatively connected to a movable carriage 8 that can be advanced or retracted. It may be noted that thrust refers to a linear force caused by the drive system 2 and could be either a forward or reverse linear force as follows. During drilling operations, the drill string 4 is pushed or thrust forward through the earth. During the backreaming process, the drill string 4 is retracted or pulled back through the borehole. Whether thrusting or pulling back, axial movement of the carriage 8 will in turn cause the spindle 6 and the drill string 4 to be similarly thrust forward or pulled back, respectively. As used herein, axial movement will be understood to include advancing or thrusting, and retracting or pulling back.

The spindle 6 is mounted in carriage 8 and usually comprises an internally threaded spindle pipe joint for connection to an externally threaded end of a pipe section 9. The opposite end of the pipe section 9 then connects with an externally threaded end of another pipe section. Therefore, in the preferred embodiment a plurality of individual pipe sections 9 are connected together at the threaded pipe joints to form the drill string 4. However, the invention would be equally applicable to a drilling machine 1 using other kinds of drill strings, such as a drill string made up of pipe sections secured together in a manner other than with threaded pipe joints.

The spindle 6 is rotatable about its central longitudinal axis. The operations of making up and breaking out the connections between the spindle 6 and the end of the drill string 4, between the spindle and an individual pipe section 9, or between the pipe sections comprising the drill string, involve careful coordination between the rotation and thrust of the spindle. Whenever a connection is made ("makeup") or broken ("breakout"), the rotation and axial movement of the spindle 6 about its axis must be coordinated to generally meet the threaded pitch of the pipe sections 9 so that the threads of the pipe joints are not damaged.

In this manner, the thrust power unit 7 and the rotation power unit 5 can be selectively activated to impart rotation and thrust output to the drill string 4. However, other power units may be employed to control various other kinematic components of drill string 4 motion such as pull back at constant or varying rates of motion. Additionally, each kinematic component of drill string 4 motion may be selectively activated independently or in combination with other components. For example, thrust only can be activated, or thrust and rotation together, or rotation only.

With continued reference to FIG. 2, the pipe handling device 3 is used to extend the length of the drill string 4 as the drill string is advanced through the earth. In the preferred embodiment, the pipe handling device 3, adds and removes threaded pipe sections 9 to and from the drill string 4 in make-up and break-out operations. Preferred embodiments for suitable pipe handling devices are described in U.S. Pat. No. 6,179,065, issued Jan. 30, 2001, entitled System and Method for Automatically Controlling a Pipe Handling System for a Horizontal Boring Machine, and U.S. Pat. No. 6,085,852, issued Jul. 11, 2001, entitled Pipe Handling Device. The contents of both patents are incorporated herein by reference.

With reference again to FIG. 1, the drilling machine 1, further comprises a machine control system 10. The machine control system 10 automatically coordinates the operations of the pipe handling device 3 with the drilling machine 1 operations. For example, electrical circuits, sequence valves, control valves, switches or computer processes may be used to automatically coordinate components of the pipe handling device 3 with that of the drilling machine 1 operations as will be described later.

Generally, the machine control system 10 is responsive to the input of a machine operator. In the preferred embodiment, the machine control system 10 maintains the operations of the drilling machine 1 at set operational levels for a desired length of time without operator intervention.

Figure 3:
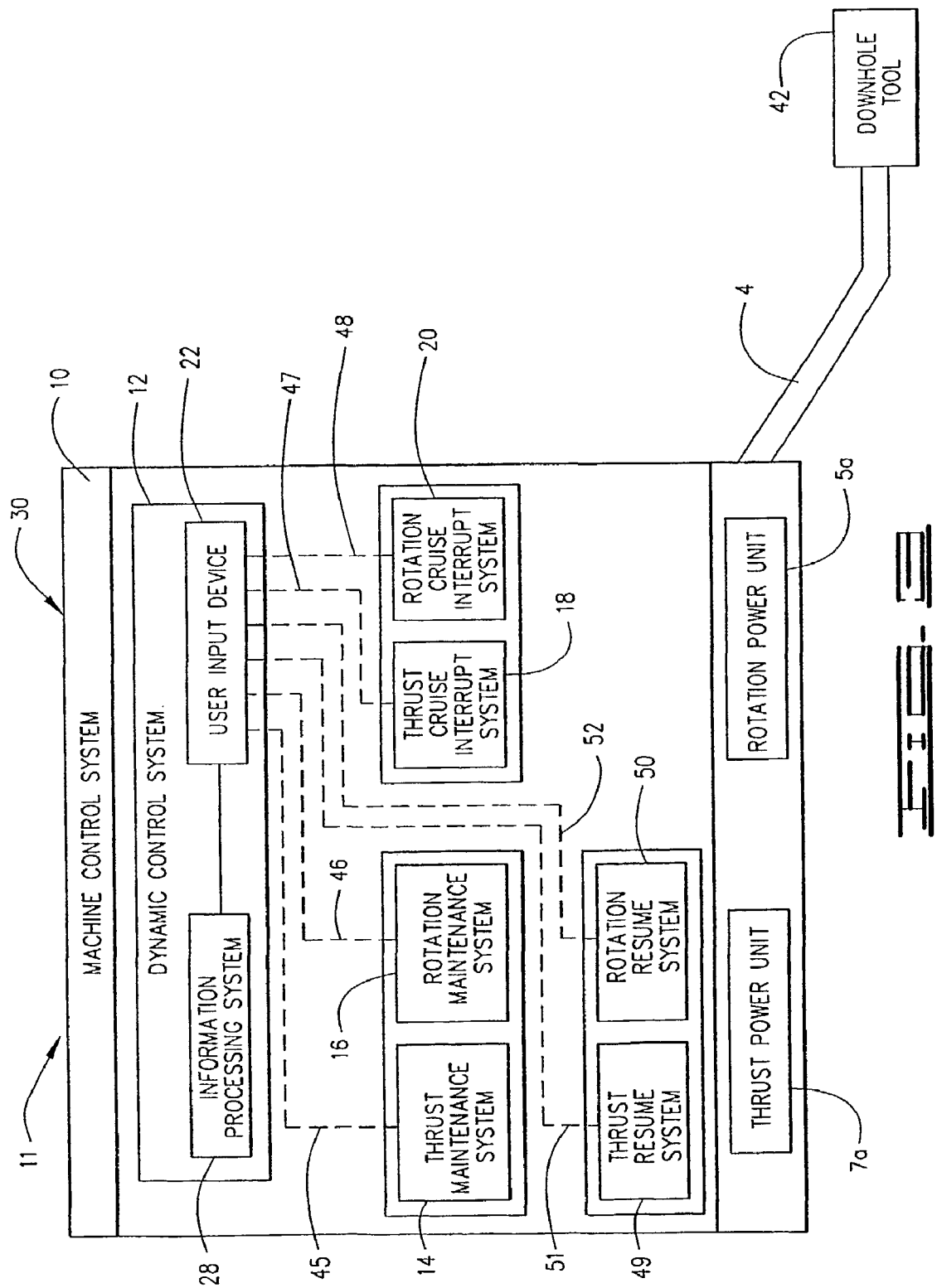
FIG. 3 is a block diagram illustrating a system for controlling an operation of a machine constructed in accordance with the present invention.

Turning now to FIG. 3, there is shown therein a system in accordance with the present invention for controlling a machine such as a horizontal drilling machine 1 which produces a thrust output and a rotation output. The system, designated by reference numeral 11, generally comprises a dynamic control system 12, a thrust rate maintenance system 14, a rotation rate maintenance system 16, a thrust interrupt system 18 and a rotation interrupt system 20.

The dynamic control system 12, preferably comprises a user input device 22, sensors (not shown) that interpret the position of the user input device and send a signal (not shown) to an information processing system 28. Upon detection of the signal, the information processing system 28 relays a control signal (not shown) such as a thrust input signal and a rotation input signal to a power source in a manner yet to be described. As used herein, the power source is intended to refer to any source of power capable of supplying the thrust and rotation outputs of a machine 30. For example, the rotation output is powered by a rotation power unit 5 and the thrust output is powered by a thrust power unit 7. As stated earlier, the rotation power unit 5 and the thrust power unit 7 can be, for example, hydraulic motors together with their power source, each respectively operably connected by way of the dynamic control system 12. The hydraulic motor output side of the thrust power unit 7 could instead be a hydraulic cylinder that is responsive to pressurized hydraulic fluid. Other arrangements of fluid, electrical or mechanical devices can be equivalently employed in the alternative.

Preferably, the user input device 22 is manually operable and can be manipulated by an operator of the system. For example, the user input device 22 may be a two-axis joystick, multiple control levers, control knobs, numeric keypad, or any other device that can input the operator desired initial and subsequently updated thrust and rotation operational levels. It may be noted that while the user input device 22 described in connection with the dynamic control system 12 is manually operable, it is to be understood that the present invention can readily be adapted wherein the input device is operated automatically.

Figure 4:
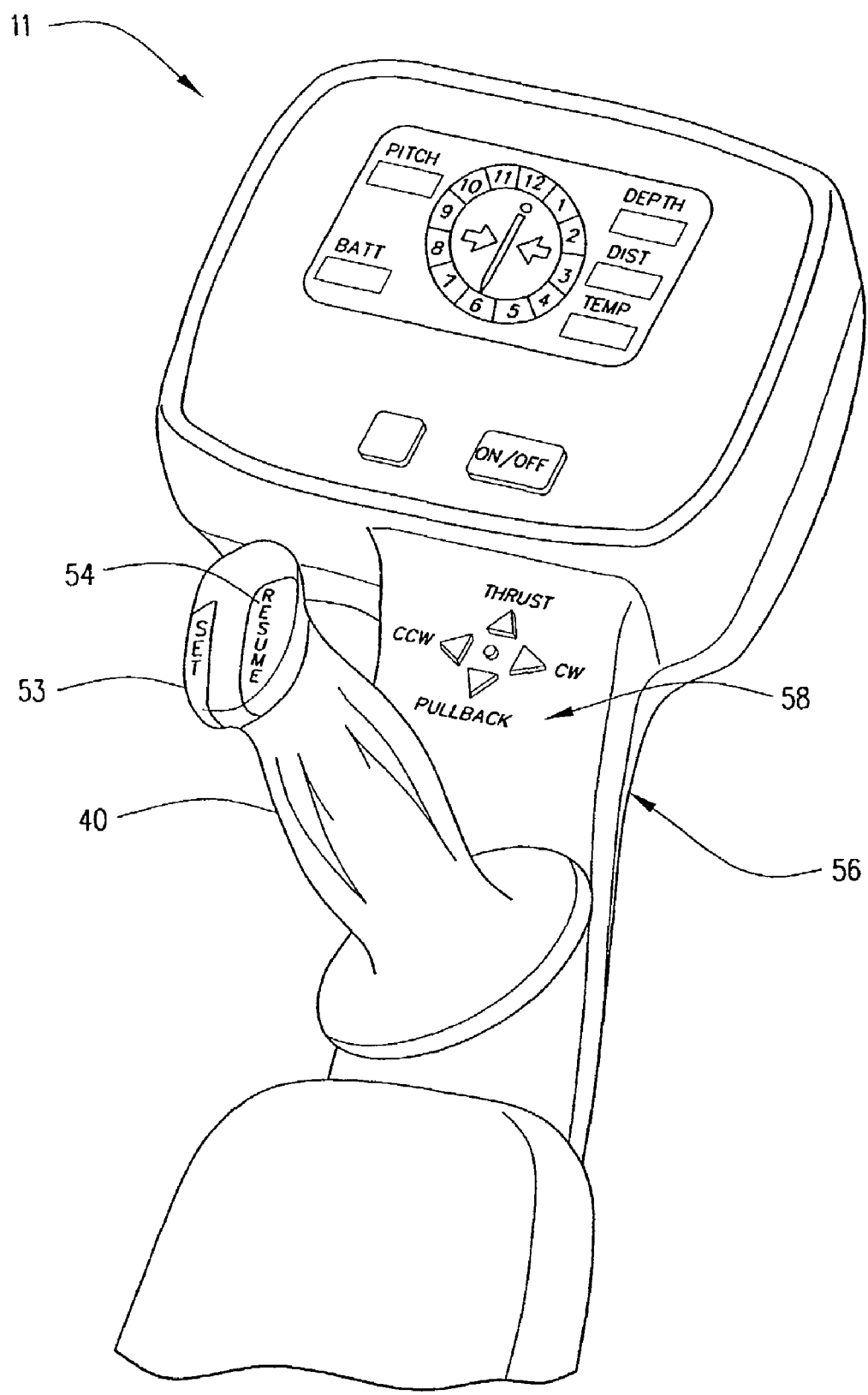
FIG. 4 is an isometric view of a joystick control constructed in accordance with an embodiment of the present invention wherein the set and resume switches are integral to the joystick.

With reference to FIG. 4, there is shown therein a preferred embodiment of the user input device 22, such as the joystick 40. The joystick 40, when used in accordance with the present invention, automatically regulates the thrust output in response to the thrust input signal and rotation output of a machine in response to the rotation input signal wherein the machine is for example, the horizontal drilling machine 1 (FIG. 1). The horizontal drilling machine 1 as stated earlier, is adapted to move the drill string 4 with a downhole tool 42 along the subsurface path. The drilling machine 1 produces an output having a plurality of kinematic components, with each such output component responsive to a corresponding component input signal. Examples of kinematic components include thrust, rotation, pullback, etc. Each output component may be produced singly or in combination in response to the corresponding input signals that are also produced either singly or in combination as will be described later. Generally, the joystick 40, as depicted in FIG. 4 operates by taking a mechanical movement or input from the operator of the horizontal drilling machine 1 and translating that into an electrical output. This output is most often an electrical voltage level, and, as stated earlier, this output is normally linearly related to the input. However, some joysticks can also produce a non-linear response. The input-output translation can be accomplished in a number of ways. For example, the position of the joystick may move a potentiometer (a device that changes resistance based on relative movement). Another method preferable is that the position of the joystick is sensed by Hall effect sensors. The Hall effect sensors measure movement by the changes in magnetic field when movement occurs. This measurement of joystick movement is converted by way of, for example, a microprocessor into a voltage input, which is transmitted to the hydraulic pump controllers or control valves. The pump controllers or control valves react proportionally to the input. This reaction includes for example, changing the volume output of the pump or changing the position of the valve to result in a different hydraulic flow from the pump or through the valve. The newly adjusted hydraulic flow results in a change in motor speed that is directly related to output speed of thrust or rotation as will be described.

With continued reference to FIG. 4, there is shown therein the preferred joystick 40 supported on a console 56. The thrust and rotation input signals are each regulated by a user manipulation of the joystick 40 as follows. The console 56 is provided with indicia 58 corresponding to outputs associated with the positioning of the joystick 40 based on the dynamic input from the operator of the horizontal drilling machine 1. For example, a forward movement of the joystick 40 produces a thrusting action on the drill string. As the joystick 40 is moved farther forward, the resulting thrust rate increases. Similarly, a rearward movement of the joystick 40 produces a pull back action on the drill string 4, such as is required during backreaming. A left or right side movement of the joystick 40 results in a clockwise or counterclockwise rotation of the drill string 4, respectively. The joystick is biased to return to a central neutral position when released from any given position.

Preferably, as illustrated in FIG. 3, the user input device 22 is further adapted wherein user manipulation of the user input device generates a thrust maintenance signal 45 and a rotation maintenance signal 46 to activate the thrust maintenance system 14 and the rotation maintenance system 16. Additionally, the thrust interruption system 18 and the rotation interruption system 20 are similarly activated in response to generation of a thrust interrupt signal 47 and a rotation interrupt signal 48 respectively, in response to user manipulation of the same user input device 22 such as the joystick 40. Preferably, the user input device 22 is also designed to activate a thrust resume system 49 and a rotation resume system 50 in response to a thrust resume signal 51 and a rotation resume signal 52 respectively, that are generated in response to user manipulation of the user input device 22 as will be described.

With reference to FIG. 3, the thrust maintenance system 14 and the rotation maintenance system 16 are activated by the user input device 22 to automatically maintain the thrust input signal and the rotation input signal respectively. The thrust input signal and rotation input signal are maintained at a user-selected thrust maintenance level in response to the thrust maintenance signal 45 and a user-selected rotation maintenance level in response to a rotation maintenance signal 46, respectively, in a manner yet to be described.

The thrust maintenance system 14 and the rotation maintenance system 16 may be two separate systems or, in the alternative, a single system performing the combined function of maintaining the thrust input signal and the rotation input signal at user selected maintenance levels for thrust and rotation, respectively. Additionally, each system may be activated independent of the other or, in the alternative, both may be activated together. The thrust maintenance system 14 and the rotation maintenance system 16, for example, may be individual or combined switches, knobs, levers, keypads, or any other types of devices capable of maintaining the thrust input signal and the rotation input signal in response to receiving the thrust maintenance signal 45 and rotation maintenance signal 46, respectively, as previously stated.

Once the thrust maintenance system 14 and the rotation maintenance system 16 are activated, the rotation and thrust signals are maintained by the said maintenance systems and by allowing the user input device 22 to return to a neutral position at which no input from the input device is required for the machine 30 to continue to function at the saved operational levels as discussed below.

In the preferred embodiment illustrated in FIG. 4, the user input device 22 also comprises the input to thrust and rotation maintenance system 14 and 16 respectively, in the form of, for example, a set switch 53. The set switch 53 may be provided as an integral part of the joystick 40. Alternatively, the set switch 53*a* may be separate from the joystick 40*a* as illustrated in FIGS. 5 and 6.

Figure 5:
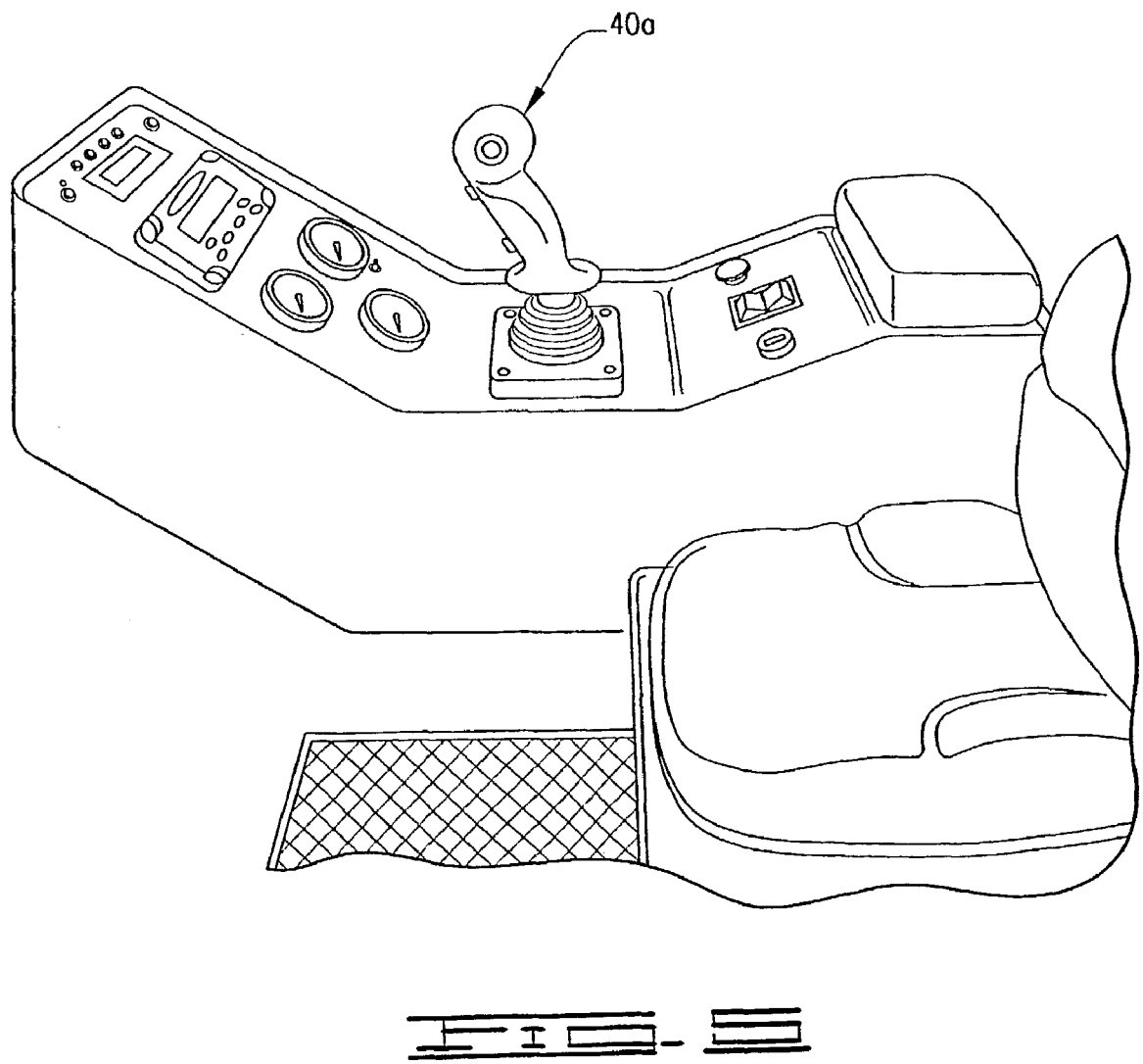
FIG. 5 is an isometric view of a joystick control constructed in accordance with another embodiment wherein the set and resume switches are separately provided in a control panel.
Figure 6:
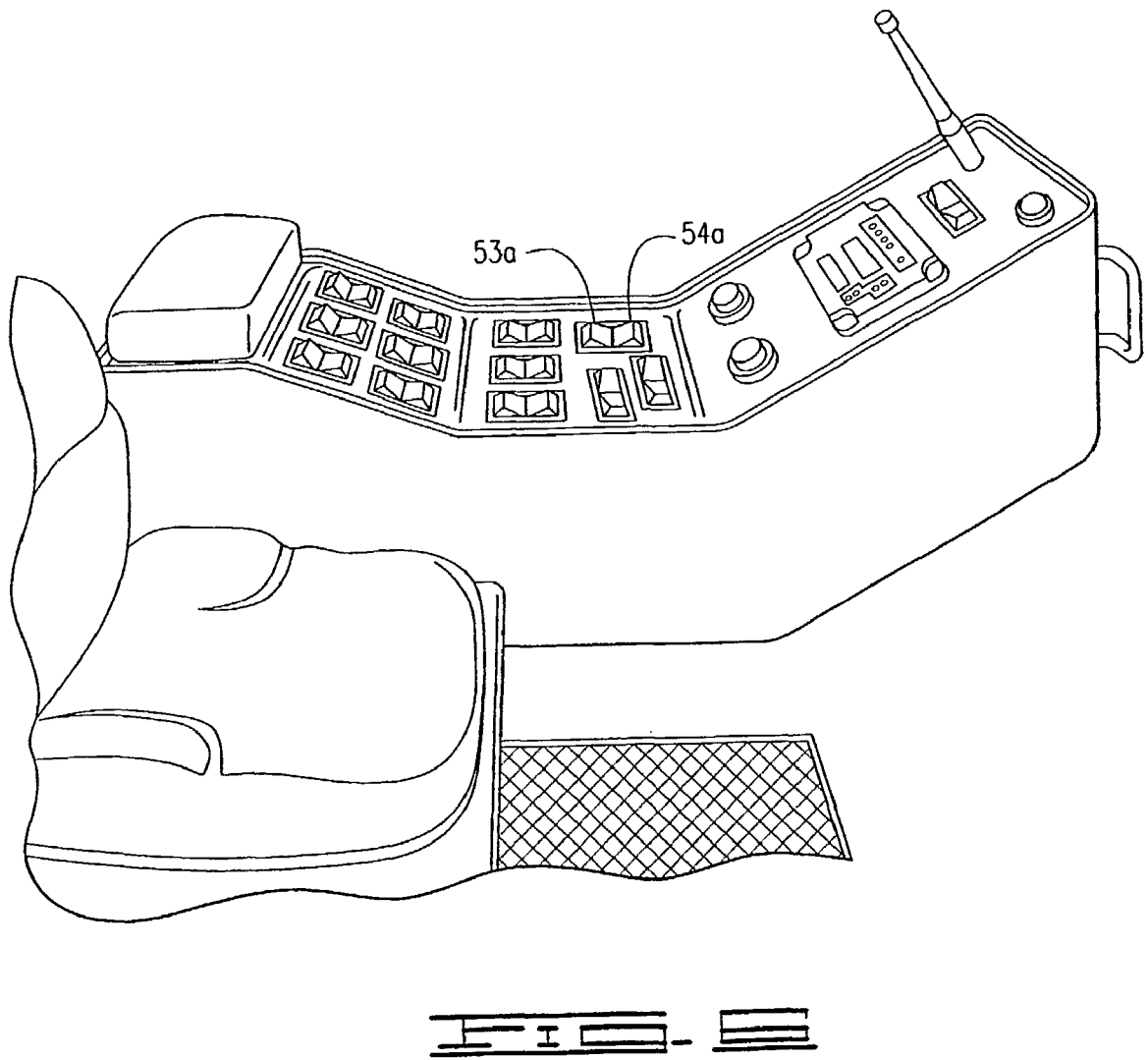
FIG. 6 is an isometric view of the set and resume switch of the joystick control of FIG. 5.

In the preferred embodiment, the thrust and rotation maintenance systems 14 and 16, are initiated by activation of the set switch shown as switch 53 and 53*a* of FIGS. 4-6, such as by user manipulation of the set switch. For example, by pushing down on the set switch. However, other modes of activation such as lifting up on the switch, entering numbers on a keypad switch, inserting a key into a keypad, moving a lever, etc., may be alternatively used. Activation of the set switch 53 serves two main functions. The first function that the set switch 53 serves is to initiate the thrust maintenance system 14 and the rotation maintenance system 15 to fix or maintain the desired operational levels after the operational levels have been set into the user input device 22, such as through positioning of the joystick 40 by the operator of the machine 30. Additionally, the set switch 53 serves to decrement the rotation operation levels and/or decrement the thrust operational levels and thus set a new maintenance signal level for the rotation and/or thrust maintenance signal. This is done if the desired thrust or rotation maintenance levels are less than the current maintained operational levels for the thrust input signal and the rotation input signal respectively.

However, if a thrust or rotation input signal greater than the maintained operational levels is required, the system 11 employs the thrust resume system 49 and the rotation resume system 50, as illustrated in FIG. 3. The thrust resume system 49 and the rotation resume system 50 are actuated by the user input device 22 to restore automatic maintenance of the thrust input signal and the rotation input signal respectively. The thrust input signal is increased above or resumed to the preselected operational level in response to the thrust resume signal 51 from the user input device 22. Similarly, the rotation input signal is increased above or resumed to the preselected operational level in response to the rotation resume signal 52 from the user input device 22 in a manner yet to be described.

The thrust resume system 49 and the rotation resume system 50 may be two separate systems or in the alternative, a single system performing the combined function of resuming thrust and rotation input signals to the preselected operational levels. The thrust resume system 49 and the rotation resume system 50, for example, may be individual or combined switches, knobs, levers, keypads, or any other types of devices capable of resuming the thrust and rotation input signals in response to receiving the thrust resume signal 51 and the rotation resume signal 52, respectively. Additionally, in the preferred embodiment, the thrust resume system 49 and the rotation resume system 50 may be activated independently of the other, or in the alternative, the two systems may be activated simultaneously in response to simultaneous generation of the thrust resume signal 51 and rotation resume signal 52 from the user input device 22.

In the preferred embodiment shown in FIG. 4, the user input device 22 comprises the thrust and rotation resume systems 49 and 50, respectively, in the form of, for example, a resume switch 54. Preferably, the resume switch 54 is provided as an integral part of the joystick 40. Alternatively, the resume switch 54*a* is provided separately from the joystick 40*a* as illustrated in FIGS. 5 and 6.

In the preferred embodiments illustrated in FIGS. 4-6, the thrust and rotation resume systems 49 and 50 are activated by user manipulation, such as by pushing down on the resume switch 54. However, other modes of activation such as lifting up on the switch, entering numbers on a keypad, inserting a key into a keypad, moving a lever, etc. may be alternatively employed. Activation of the resume switch 54 serves two main functions. First, the resume switch 54 serves to resume the preselected operational levels where these levels had already been previously set up. Additionally, the resume switch 54 serves to readjust the operational levels for the thrust input signal and the rotation input signal where the thrust input signal and rotation input signal is desired to be greater than the preselected maintained operational level as described herein.

FIG. 7 illustrates an electronic and hydraulic schematic for a system 11 constructed in accordance with the present invention for controlling the machine 30. The system 11 illustrates use of a user input device 22, comprising a joystick 40, a set switch 53, and a resume switch 54. The joystick 40, set switch 53, and resume switch 54 are operatively connected to a processor 60 which, in turn, controls the speed and direction of the thrust power unit 7 and the rotation power unit 5. The processor 60 has numerous functions. For example, cruise control, driving control, drilling/backreaming control, etc. The processor 60 may be, for example, any computer capable of taking input from various switches, sensors, levers, joystick, etc. and together with programming logic, sending out the desired signals to control various functions. The system 11 of FIG. 7 is illustrative only of the spirit of the present invention, and obvious equivalents can be constructed. For example, FIG. 7 illustrates a number of hydraulic pumps 68, 70, 72 as fixed displacement type pumps, although variable displacement pumps could be used as well.

Preferably, the joystick 40 is operatively connected to a sensor 134 that detects the pivotal position of the joystick 40 as it is moved by the operator in guiding the drill string 4. The set switch 53 and resume switch 54 are also operatively connected to the processor 60. The mode of operation for the system in question works as follows. The operator preferably controls the system through the joystick 40. The operator inputs the desired operational level for rotation and thrust through the joystick 40. The joystick 40 has sensors 134 that interpret the position of the joystick and send a joystick signal 136 to the processor 60. The processor 60 detects the joystick signal 136 and either sends a control signal 150, the thrust input signal for forward thrust to a thrust valve 152 to go in the forward direction, or a control signal 151, the thrust input signal for pullback, to the thrust valve 152 to go in the pullback/reverse direction. The thrust valve control head 153, which receives hydraulic pressure from hydraulic pump 72, upon receipt of the control signal 150 or 151 moves to apply hydraulic pressure to either the control line 156 or 154 respectively, to shift the main thrust spool 162. The pressure in control line 154 acts upon the end 158 of the main thrust spool 162 in order to shift it in the pullback/reverse direction. The pressure in control line 156 acts upon the end 160 of the main thrust spool 162 in order to shift it in the forward direction. The main thrust spool 162 receives hydraulic fluid from hydraulic pump 68 and sends hydraulic fluid to the thrust power motor 64 to cause the carriage to move.

The same is also true for rotation. The processor 60 detects the joystick signal level 136 and sends a control signal 164, the rotation input signal for clockwise rotation, to a rotation valve 166 to go in the clockwise direction, or a control signal 167, the rotation input signal for counterclockwise rotation, to the rotation valve 166 to go in the counterclockwise direction. The rotation valve control head 168, which receives hydraulic pressure from hydraulic pump 72, upon receipt of the control signal 164 or 167 moves to apply hydraulic pressure to either the control line 172 or 170 respectively, to shift the main rotation spool 174. The pressure in control line 170 acts upon the end 176 of the main rotation spool in order to shift in the counterclockwise direction. The pressure in control line 172 acts upon the end 178 of the main rotation spool in order to shift in the clockwise direction. The main rotation spool 174 receives pressure from hydraulic pump 70 and sends hydraulic fluid to the rotation power motor 66 to cause the spindle to rotate.

To operate the maintenance control system 11, the operator inputs the desired operational level for thrust and rotation through the joystick 40. The operator then depresses the set switch 53 and a set switch signal 179 is sent to the processor 60. The processor 60 detects the joystick signal 136 and the set switch signal 179. It then maintains the control signal level 150 or 151 and the control signal level 164.

To adjust the operational level setting, the operator must actuate the set switch 53 or resume switch 54. Pressing the set switch 53 will function to decrease or decrement the operational level of the machine 30. The set switch signal 179 is detected by the processor 60 when the set switch 53 is actuated, and the joystick signal 136 is checked to determine the location of the joystick 40. If the joystick 40 is in neutral, the control signal 150 or 151 is reduced to lower the thrust or pullback operational level respectively. If the joystick 40 is in the clockwise rotation direction, the control signal 164 is reduced to lower the rotation operational level.

Pressing the resume switch 54 will function to increase the operational settings. A resume switch signal 180 is detected by the processor 60 when the resume switch 54 is actuated, and the joystick signal 136 is checked to determine the position of the joystick 40. If the joystick 40 is in neutral, the control signal 150 or 151 is increased to raise the thrust or pullback operational level respectively. If the joystick 40 is in the clockwise rotation direction, the control signal 164 is increased to raise the rotation operational level.

When the operator chooses to override the operational levels for thrust or rotation, the joystick 40 is actuated. The joystick signal 136 is detected by the processor 60 and checked to see what direction the joystick 40 is actuated in. If the joystick 40 is placed in a thrust or pullback direction, then the control signal 150 or 151 is increased to match the new operational level. If the joystick 40 is placed in a clockwise rotation direction, then the control signal 164 is increased to match the new operational level. When the joystick 40 is returned to the neutral position, the processor 60 detects the change in joystick signal 136 and changes the control signal 150, 151, or 164 back to its original level.

To interrupt the maintenance control system 11, the operator must actuate joystick 40 in the opposite direction to which the carriage is travelling. The processor 60 detects this in joystick signal 136 and reduces control signal 150 or 151 and control signal 164 to zero. To resume cruise control, the operator moves the joystick 40 which produces the joystick signal 136 detected by the processor 60 and pushes the resume switch 54 that produces signal 180 detected by the processor 60. The processor 60 then reestablishes control signal level 150 or 151 and control signal level 164 to its previous levels.

Figure 8B:
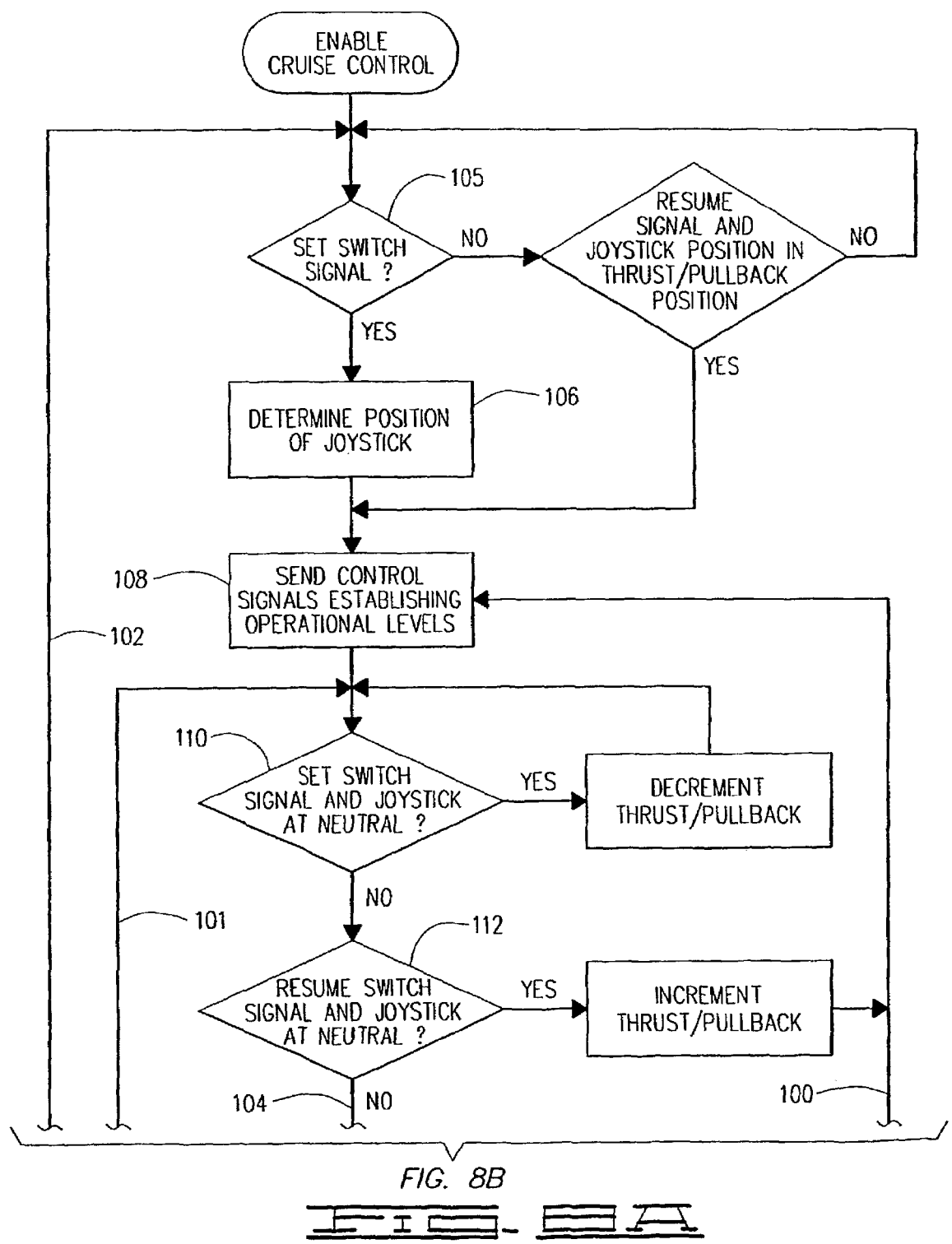
FIG. 8 is a flow chart illustrating the operation of the processor in the system of FIG. 7.

FIGS. 8A and 8B illustrate a preferable logic flowchart of the operations of an information processing system 28, such as the processor 60, constructed in accordance with the present invention. It will be noted that when the processor 60 detects the set switch signal (at 105), the position of the joystick 40 is essentially instantaneously determined (at 106). Based on the position of the joystick 40, the processor 60 sends input signals, such as control signals 150 or 151 and/or 164 to the valves 152 and/or 166 respectively. Thereafter, the established operational level is maintained as control is passed to block 108 even after the operator releases the joystick 40 and it returns to the neutral position.

After enabling the system 11 as above, the thrust/pull back input signals 150 and 151 respectively, can be decremented below (at 110) or incremented above (at 112) the previously established operational level. Similarly, the rotation input signal 164 can be decremented below (at 114) or incremented above (at 116) the previously established operational level. Additionally, an override of the previously established operational level can be performed (at 118). Finally, the system 11 can be disengaged (at 120) and re-engaged after disengagement (at 194, shown in FIG. 9) as described in detail below.

Disengagement of the system 11 preferably requires activation of the thrust interrupt system 18 and the rotation cruise interrupt system 20. With reference to FIG. 3, the thrust interrupt system 18 and the rotation cruise interrupt system 20 are activated by the user input device 22. Once activated, the thrust interrupt system 18 and rotation interrupt system 20 will discontinue the automatic maintenance of a component input signal, such as the thrust input signal 150 or 151 and rotation input signal 164, in response to the thrust interrupt signal 47 and the rotation interrupt signal 48, respectively.

The thrust interrupt system 18 and the rotation interrupt system 20 may be two separate systems or in the alternative, a single system performing the combined function of discontinuing the automatic maintenance of both thrust and rotation values. The thrust interrupt system 18 and the rotation interrupt system 20, for example, may be individual or combined switches, knobs, levers, input keypads, or any other type of devices capable of discontinuing the automatic maintenance of the thrust and rotation values in response to receiving the thrust interrupt signal 47 and the rotation interrupt signal 48 as previously stated. Additionally, in the preferred embodiment, the thrust cruise interrupt system 18 and the rotation interrupt system 20 may be activated independently of the other, or in the alternative, the two systems may be activated simultaneously.

In the preferred embodiment, the user input device 22 comprises the thrust and rotation interrupt systems 18 and 20 respectively, as an integral part of the joystick 40 controls. Preferably, the joystick 40 is manipulated by the user of the machine 30 to a position and direction that is opposite of the direction of travel of the drill string 4 prior to activation of the thrust and rotation interrupt system. For example, during drilling operations, if the drill string 4 was being thrust forward or moved forward by pushing the joystick 40 in the positive Y direction, then pulling the joystick 40 back in the negative Y direction will discontinue the automatic maintenance of the thrust maintenance system. Conversely, if during backreaming the drill string 4 was being pulled back out of the borehole with a pullback value by pulling the joystick 40 in the negative Y direction, then thrusting the joystick 40 forward in the positive Y direction will discontinue the automatic maintenance of a pullback maintenance system (not shown).

In the preferred embodiment, to resume the preselected thrust input signal and rotation input signal operational levels after the thrust maintenance system 14 and the rotation maintenance system 16 has been disengaged, the joystick 40 is positioned in the preferred direction of movement and the thrust resume system 49 and the rotation resume system 50, such as the resume switch 54 or 54a, is activated. Preferably, once the resume switch 54 or 54a is activated, the joystick 40 can be released and the machine 30 will return to the last preselected operational levels.

Figure 9B:
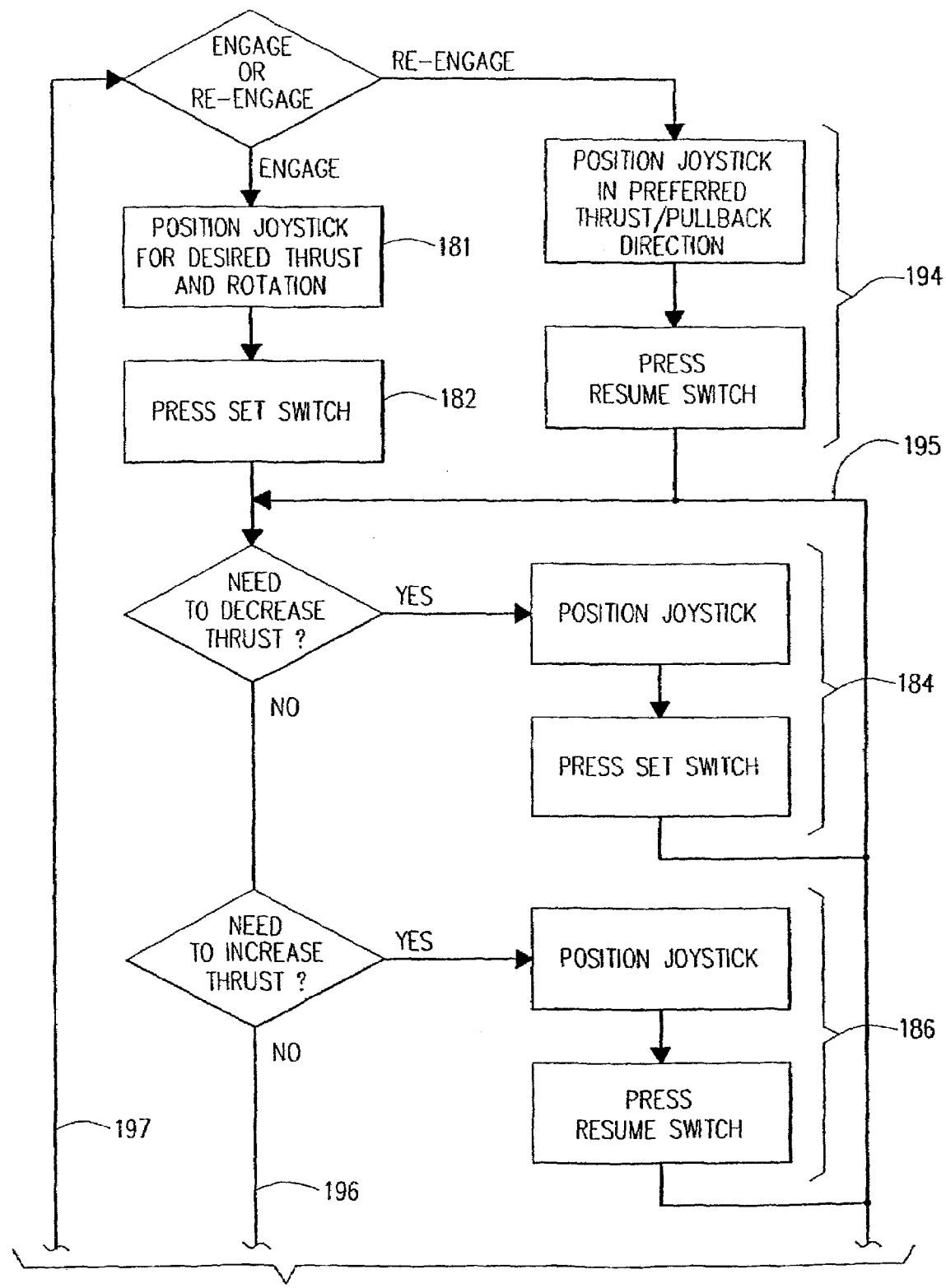
FIG. 9 is a block diagram illustrating the method of operation of the present invention.
Figure 9B:
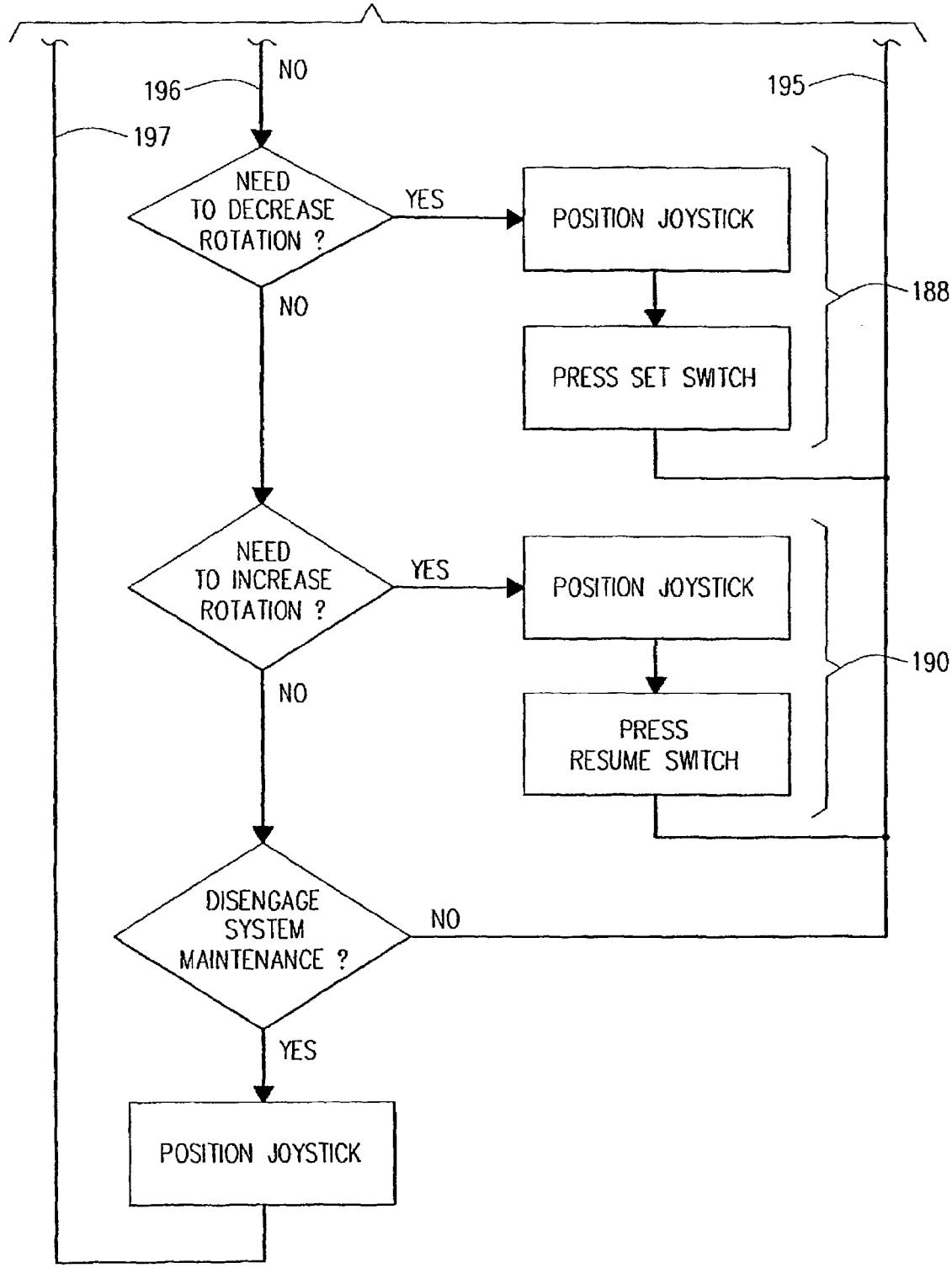

FIG. 9 is a block diagram illustrating the method steps that an operator follows to adjust the operational level of any desired component input signal such as thrust and rotation either independently or together once the system 11 has been engaged. To engage the control system 11, the operator positions the joystick 40 so that thrust or pullback and the rotation are at the desired operational levels at 181 and then depress the set switch 53 at 182. The joystick 40 can then be released to neutral and the machine will continue to function proportionally at these operational levels. The operator can then independently adjust either function's operational level.

To adjust the thrust or pullback operational level, the operator must use only the set switch 53 or the resume switch 54. To decrease the thrust or pullback operational level, the operator must depress the set switch 53 while the joystick 40 is in the neutral position at 184. To increase the thrust or pullback operational level, the operator must depress the resume switch 54 while the joystick 40 is in the neutral position at 186. To adjust the rotation operational level, the operator must use the joystick 40 and set switch 53 or the resume switch 54. Alternatively, separate switches could be used to adjust rotation and thrust. To decrease the rotation operational level, the operator must move the joystick 40 out of neutral in the clockwise rotation direction only and depress the set switch 53 at 188. To increase the rotation operational level, the operator must move the joystick 40 out of neutral in the clockwise rotation direction only and depress the resume switch 54 at 190.

To override the operational level, the operator can move the joystick 40 out of neutral to a position exceeding the current operational level of either function and the unit will increase to that level. After releasing the joystick 40, the unit will return to the preset operational level. If preferred, the control can be set for thrust only and rotation will continue to remain in operator control. In this mode, the joystick 40 would be moved out of neutral in the thrust or pullback direction to the desired operational level and the set switch 53 depressed. Then the joystick 40 would be returned to neutral with the operator controlling the rotation operational level and direction as normal.

To disengage the system 11, the joystick 40 must be moved out of neutral to a position that is opposite of the direction the carriage 8 is traveling at 192. If it is thrusting, pulling back on the joystick 40 will disengage the system 11 and if it is pulling back, pushing the joystick forward will disengage it. To resume system 11 control after disengaging it, the joystick 40 must be positioned out of neutral in the preferred direction of movement and the resume switch 54 depressed at 194. The joystick 40 can then be released and the unit will return to the last operational levels it was running at. Additionally, before system 11 control is ever engaged, a few checks are performed to ensure correct operating conditions such as the front wrench being open, shuttles being retracted, and drill mode being on.

It may be noted that the operational levels referred to in this description are the electrical control signals sent to the thrust and rotation power unit controllers or control valves. The controlled levels could be expanded to include actual levels of thrust or rotation rate and thrust or rotation pressure and could employ feedback sensors and control logic to maintain them. To achieve specific levels of thrust and rotation rate, speed pickup type devices could be placed on the thrust and rotation power units 5 and 7, respectively. These speed pickup devices would produce a signal that is indicative of the actual speed of thrust and rotation of the machine 30. The system 11 can then maintain operator-selected speeds by adjusting the electrical control signals to the thrust and rotation power units 5 and 7, respectively. That is, speed would then be the operational level that the system 11 is maintaining and not the electrical control signals.

Additionally, pressure sensors could be added to the thrust and rotation power units 5 and 7, respectively, to produce a signal indicative of the pressure in these systems which is indicative of the forces developed by these systems, respectively. In this case, the system 11 works as above, maintaining the operator-selected pressure levels by adjusting the electrical control signals to the thrust and rotation power units 5 and 7, respectively. Additionally, with the speed pickup on the thrust power unit 7, the system 11 can track where a carriage 8 (not shown) of the machine 30 is at all times. In this manner, the system 11 would have certain count levels that correspond with certain important positions of the carriage 8 like the required position to either add or remove pipe sections 9 from the drill string 4. When the carriage 8 reached the count levels that represented these positions, the rate maintenance system could be made to disengage automatically to stop and add a pipe section 9 or remove a pipe section 9 from the drill string 4.

It is clear that the present invention is well adapted to attain the ends and advantages mentioned as well as those inherent therein. While the presently preferred embodiments of the invention have been described for purposes of the disclosure, it will be understood that numerous changes may be made which will readily suggest themselves to those skilled in the art and which are encompassed within the spirit of the invention disclosed.

What is claimed:

1. A system for controlling a horizontal drilling machine which produces a thrust output in response to a thrust input signal and a rotation output in response to a rotation input signal, comprising:
    a dynamic control system for the horizontal drilling machine adapted to regulate the thrust input signal and the rotation input signal in response to dynamic user input, the dynamic control system comprising at least one manually operable user input device;
    a thrust maintenance system adapted to automatically maintain the thrust input signal at a user-selected thrust maintenance level in response to a thrust maintenance signal;
    a rotation maintenance system adapted to automatically maintain the rotation input signal at a user-selected rotation maintenance level in response to a rotation maintenance signal;
    a thrust interrupt system adapted to discontinue automatic maintenance of the thrust input signal in response to a thrust interrupt signal;
    a rotation interrupt system adapted to discontinue automatic maintenance of the rotation input signal in response to a rotation interrupt signal; and
    a thrust resume system adapted to restore automatic maintenance of the thrust input signal to the previous selected thrust maintenance level in response to a thrust resume signal;
    wherein the thrust interrupt signal is generated in response to a user manipulation of the at least one manually operable user input device during a drilling operation.

2. The system of claim 1 wherein the thrust maintenance system and the rotation maintenance system are actuable independently of one another.

3. The system of claim 1 wherein the thrust interrupt system and the rotation interrupt system are actuable independently of one another.

4. The system of claim 1 further comprising a rotation resume system adapted to restore automatic maintenance of the rotation input signal to the previous selected rotation maintenance level in response to a rotation resume signal.

5. The system of claim 1 wherein the rotation interrupt signal is generated in response to the same user manipulation which causes generation of the thrust interrupt signal.

6. The system of claim 1 wherein the rotation interrupt signal is generated in response to a user manipulation of the same at least one manually operable user input device.

7. The system of claim 6 wherein the thrust interrupt signal is generated in response to the same user manipulation which causes generation of the rotation interrupt signal.

8. The system of claim 1 wherein the thrust and rotation input signals are each regulated by a user manipulation of the same at least one manually operable user input device.

9. The system of claim 8 wherein each of the thrust maintenance and rotation maintenance signals are each generated in response to a user manipulation of the same at least one manually operable user input device.

10. The system of claim 8 wherein each of a thrust resume signal and a rotation resume signal are generated in response to a user manipulation of the same at least one manually operable user input device.

11. The system of claim 10 wherein the thrust resume signal and the rotation resume signal are generated simultaneously in response to user actuation of the same at least one manually operable input device to the resume position.

12. A system for controlling a horizontal drilling machine adapted to drivingly engage a drill swing having a downhole tool, the horizontal drilling machine producing an output having a plurality of kinematic components, with each such output component responsive to a corresponding component input signal, comprising:
- a dynamic control system for the horizontal drilling machine adapted to regulate each component input signal in response to dynamic user input, the dynamic control system comprising at least one manually operable user input device;
- a component maintenance system adapted to automatically maintain at least one component input signal at a user-selected component maintenance level in response to a component maintenance signal;
- a component interrupt system adapted to discontinue automatic maintenance of said component input signal in response to a component interrupt signal; and
- a component resume system adapted to restore automatic maintenance of said each component input signal to the previous selected maintenance level for the same component input signal in response to a component resume signal;
- wherein the component maintenance signal is generated in response to a user manipulation of the same at least one manually operable user input device; and
- wherein the component interrupt signal is generated in response to a user manipulation of the same at least one manually operable user input device during a horizontal drilling operation.

13. The system of claim 12 wherein the component input signal is a thrust input signal.

14. The system of claim 12 wherein the component input signal is a rotation input signal.

15. The system of claim 12 wherein the component input signals are a thrust input signal and a rotation input signal.

16. The system of claim 15 wherein the component maintenance system comprises a thrust maintenance subsystem adapted to automatically maintain the thrust input signal at a user-selected thrust maintenance level in response to a thrust maintenance signal.

17. The system of claim 16 wherein the component interrupt system comprises a thrust interrupt subsystem adapted to discontinue automatic maintenance of the thrust input signal in response to a thrust component interrupt signal.

18. The system of claim 16 wherein the maintenance system further comprises a rotation maintenance subsystem adapted to automatically maintain rotation input signal at a user-selected rotation maintenance level in response to a rotation component maintenance signal.

19. The system of claim 18 wherein the component interrupt system further comprises a rotation interrupt subsystem adapted to discontinue automatic maintenance of the rotation input signal in response to a rotation component interrupt signal.

20. The system of claim 19 wherein the thrust interrupt subsystem and the rotation interrupt subsystem are actuable independently of one another.

21. The system of claim 18 wherein the thrust maintenance subsystem and the rotation maintenance subsystem are actuable independently of one another.

22. The system of claim 12 wherein the component resume system comprises a thrust resume subsystem adapted to restore automatic maintenance of the thrust input signal to the previous selected thrust maintenance level in response to a thrust component resume signal.

23. The system of claim 22 wherein the component resume system further comprises a rotation resume subsystem adapted to restore automatic maintenance of the rotation input signal to the previous selected rotation maintenance level in response to a rotation component resume signal.

24. The system of claim 23 wherein the thrust resume subsystem and the rotation resume subsystem are actuable independently of one another.

25. The system of claim 12 wherein said each component input signal is regulated by a user manipulation of the same at least one manually operable user input device.

26. A system for controlling a horizontal drilling machine adapted to drivingly engage a drill string having a downhole tool, the horizontal drilling machine producing an output having a plurality of kinematic components, with each such output component responsive to a corresponding component input signal, comprising:
- a dynamic control system for the horizontal drilling machine adapted to regulate each component input signal in response to dynamic user input, the dynamic control system comprising at least one manually operable user input device;
- a component maintenance system adapted to automatically maintain at least one component input signal at a user-selected component maintenance level in response to a component maintenance signal; and
- a component interrupt system adapted to discontinue automatic maintenance of said component input signal in response to a component interrupt signal generated by operation of the user input device during a horizontal drilling operation;
- wherein said each component input signal is resumed in response to a component resume signal generated by a user manipulation of the same at least one manually operable user input device.

27. A system for controlling a drilling machine having a pipe handling assembly for adding and removing a plurality of pipe sections from a drill string, the machine producing a thrust output in response to a thrust input signal and a rotation output in response to a rotation input signal, comprising:
- a dynamic control system adapted to regulate the thrust input signal and the rotation input signal in response to dynamic user input;
- a maintenance system adapted to automatically maintain at least one of the rotation input signal and the thrust input signal at a user-selected maintenance level for the same input signal in response to a maintenance signal;
- an interrupt system adapted to discontinue automatic maintenance of said at least one of the rotation input signal and the thrust input signal in response to an interrupt signal; and
- a resume system adapted to restore automatic maintenance of the said at least one of rotation input signal and thrust input signal to the previous selected maintenance level for the same input signal in response to a resume signal;
- wherein the interrupt signal is generated in response to a makeup/breakout signal from the pipe handling assembly.

28. The system of claim 27 wherein the maintenance system is adapted to automatically maintain rotation and thrust input signals independently of one another.

29. The system of claim 27 wherein the interrupt system is adapted to discontinue automatic maintenance of rotation and trust input signals independently of one another.

30. The system of claim 27 further comprising a rate feedback system adapted to signal the user of the system at least one of an actual thrust and rotation rate of the drill string.

31. The system of claim 30 farther comprising an output feedback system adapted to signal the user of the system at least one of an actual thrust and rotation output of the drill string.

32. The system of claim 31 further comprising a pressure feedback system adapted to signal the user of the system at least one of an actual thrust and rotation pressure of the drill string.

33. The system of claim 32 further comprising a device to provide visual display of the actual thrust and rotation rate, the actual thrust and rotation output and the actual thrust and rotation pressure of the drill string.

34. The system of claim 27 wherein the pipe handling assembly adds and removes at least one of the plurality of pipe sections from the drill string when the same at least one pipe section is positioned on a carriage of the machine, and wherein the pipe handling assembly generates the pipe makeup/breakout signal when the same at least one pipe section is positioned on the carriage when adding and removing the same pipe section from the drill string.

35. A method for controlling a horizontal drilling machine having a drill string with a downhole tool which produces a thrust output in response to a thrust input signal and a rotation output in response to a rotation input signal, the method comprising:
    selecting a subsurface bore path along which the downhole tool is moved;
    axially advancing the drill string so as to move the downhole tool along at least a portion of the selected subsurface bore path;
    regulating the thrust input signal and the rotation input signal in response to a dynamic user input;
    automatically maintaining the thrust input signal at a user-selected thrust maintenance level in response to a thrust maintenance signal;
    automatically maintaining the rotation input signal at a user-selected rotation maintenance level in response to a rotation maintenance signal;
    discontinuing automatic maintenance of thrust input signal at the thrust maintenance level in response to a thrust interrupt signal;
    discontinuing automatic maintenance of rotation input signal at the rotation maintenance level in response to a rotation interrupt signal; and
    restoring automatic maintenance of the thrust input signal to the previous selected thrust maintenance level in response to a thrust resume signal.

36. The method of claim 35 wherein the step of moving the downhole tool comprises determining the location of the downhole tool along the subsurface bore path.

37. The method of claim 36 wherein the step of moving the downhole tool further comprises guiding the downhole tool substantially horizontally along the subsurface bore path in response to the determined downhole tool location.

38. The method of claim 37 wherein the step of guiding the downhole tool comprises automatically changing a direction of the downhole tool to a user selected direction along the subsurface bore path.

39. The method of claim 35 further comprising adding at least one pipe section to the drill string to extend the length of the drill string during drilling.

40. The method of claim 39 further comprising removing at least one pipe section from the drill string to reduce the length of the drill string during backreaming.

41. The method of claim 40 wherein the step of backreaming comprises drilling a pilot borehole and enlarging the borehole with a backreaming to install a utility line attached to the backreamer in the bore hole.

42. The method of claim 35 wherein the steps of automatically maintaining the thrust input signal and the rotation input signal are actuable independently of one another.

43. The method of claim 35 wherein the steps of discontinuing automatic maintenance of the thrust input signal and the rotation input signal are actuable independently of one another.

44. The method of claim 35 further comprising the step of restoring automatic maintenance of the rotation input signal to the previous selected rotation maintenance level in response to a rotation resume signal.

45. The method of claim 35 wherein the step of discontinuing the automatic maintenance of the thrust input signal comprises manipulating at least one manually operable user input device to generate the thrust interrupt signal.

46. The method of claim 45 wherein the step of discontinuing the automatic maintenance of the rotation input signal comprises performing the same user manipulations which causes generation of the thrust interrupt signal.

47. The method of claim 35 wherein the step of discontinuing the automatic maintenance of the rotation input signal comprises manipulating at least one manually operable user input device to generate the rotation interrupt signal.

48. The method of claim 47 wherein the step of discontinuing the automatic maintenance of the thrust input signal comprises performing the same user manipulations which causes generation of the rotation interrupt signal.

49. The method of claim 35 wherein the step of regulating the thrust input signal and the rotation input signal comprises manipulating at least one manually operable user input device.

50. The method of claim 49 wherein the steps of automatically maintaining each of the thrust input signal and the rotation input signal comprises manipulating the same at least one manually operable use input device to generate the thrust maintenance signal and the rotation maintenance signal.

51. The method of claim 35 wherein the steps of restoring each of the thrust input signal and rotation input signal comprises manipulating the same at least one manually operable user input device to generate the thrust resume signal and the rotation resume signal.

52. The method of claim 51 wherein the step of restoring each of the thrust input signal and rotation input signal comprises simultaneously generating the thrust resume signal and the rotation resume signal in response to user actuation of the same at least one manually operable input device.

* * * * *

UNITED STATES PATENT AND TRADEMARK OFFICE
CERTIFICATE OF CORRECTION

| | | |
|---|---|---|
| PATENT NO. | : 7,413,031 B2 | Page 1 of 1 |
| APPLICATION NO. | : 10/220465 | |
| DATED | : August 19, 2008 | |
| INVENTOR(S) | : Koch et al. | |

It is certified that error appears in the above-identified patent and that said Letters Patent is hereby corrected as shown below:

Drawing Sheet No. 3 with Fig. 3, please delete the word "CRUISE" from the object referenced by numeral 18.

Drawing Sheet No. 3 with Fig. 3, please delete the word "CRUISE" from the object referenced by numeral 20.

Drawing Sheet No. 3 with Fig. 3, please delete reference numeral "7a" and substitute therefor --7--.

Drawing Sheet No. 3 with Fig. 3, please delete reference numeral "5a" and substitute therefor --5--.

Drawing Sheet No. 12 with Fig. 9B, please insert reference numeral --192-- to "POSITION JOYSTICK" located bottom left of the drawing.

Column 2, line 21, please delete "s stem" and substitute therefor --system--.

Column 15, line 4, please delete "swing" and substitute therefor --string--.

Column 16, line 67, please delete "trust" and substitute therefor --thrust--.

Column 17, line 4, please delete "farther" and substitute therefor --further--.

Column 18, line 9, please delete "backreaming" and substitute therefor --backreamer--.

Signed and Sealed this

Twenty-third Day of December, 2008

JON W. DUDAS
*Director of the United States Patent and Trademark Office*